(12) United States Patent
Gering et al.

(10) Patent No.: US 8,121,417 B2
(45) Date of Patent: Feb. 21, 2012

(54) PROCESSING OF CONTENT-BASED COMPRESSED IMAGES

(75) Inventors: David Thomas Gering, Waukesha, WI (US); Gopal Biligeri Avinash, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 1124 days.

(21) Appl. No.: 11/725,245

(22) Filed: Mar. 19, 2007

(65) Prior Publication Data

US 2008/0232699 A1 Sep. 25, 2008

(51) Int. Cl.
G06K 9/36 (2006.01)
G06K 9/46 (2006.01)
G06K 9/34 (2006.01)

(52) U.S. Cl. ......... 382/232; 382/244; 382/173; 382/180

(58) Field of Classification Search .................. None
See application file for complete search history.

(56) References Cited

U.S. PATENT DOCUMENTS

| | | | |
|---|---|---|---|
| 5,333,212 A | | 7/1994 | Ligtenberg |
| 5,502,778 A | * | 3/1996 | Ishikawa et al. ............. 382/239 |
| 5,796,862 A | | 8/1998 | Pawlicki et al. |
| 6,144,772 A | * | 11/2000 | Garland et al. ............... 382/239 |
| 6,633,674 B1 | * | 10/2003 | Barnes et al. ................ 382/232 |
| 6,704,440 B1 | * | 3/2004 | Kump ........................... 382/132 |
| 6,771,822 B1 | * | 8/2004 | Brackett ....................... 382/232 |

(Continued)

OTHER PUBLICATIONS

Park et al. "Region-of-Interest Coding Based on Set Partitioning in Hierarchical Trees", IEEE Trans. on Circuits and Systems for Video Technology, v. 12, Feb. 2002, pp. 106-113.*

(Continued)

*Primary Examiner* — Samir Ahmed
*Assistant Examiner* — Li Liu
(74) *Attorney, Agent, or Firm* — Fletcher Yoder, P.C.

(57) ABSTRACT

A technique for prioritizing portions of compressed multi-resolution medical image data to be processed. More relevant portions of medical image data are compressed at a higher resolution than less relevant portions of medical image data. A mask is created from the image data and used to assign data compression quality factors to corresponding image blocks in the image data. The image data in each region is compressed based on their assigned quality factor. During processing of the compressed image data, the compressed image data and the mask are accessed. The mask is used to direct the processing of the compressed image data. Depending upon the application, the mask can be used to direct that the image data for the regions of most relevance be processed before the image data for the regions of lesser relevance. However, the mask can be used to direct that the image data for the regions of lesser relevance be processed before the image data for the regions of most relevance.

12 Claims, 8 Drawing Sheets

U.S. PATENT DOCUMENTS

| | | | |
|---|---|---|---|
| 6,891,973 B1 * | 5/2005 | Atsumi et al. | 382/232 |
| 6,912,319 B1 | 6/2005 | Barnes et al. | |
| 6,937,767 B1 * | 8/2005 | Burak et al. | 382/232 |
| 7,236,637 B2 | 6/2007 | Sirohey et al. | |
| 7,421,136 B2 | 9/2008 | Sirohey et al. | |
| 2002/0044696 A1 * | 4/2002 | Sirohey et al. | 382/240 |
| 2002/0090140 A1 | 7/2002 | Thirsk | |
| 2003/0026488 A1 | 2/2003 | Park et al. | |
| 2004/0008894 A1 | 1/2004 | Zeineh | |
| 2004/0022447 A1 | 2/2004 | Mukhopadhyay et al. | |
| 2004/0071356 A1 | 4/2004 | Sudharsanan et al. | |
| 2004/0264794 A1 * | 12/2004 | Nister et al. | 382/243 |
| 2007/0065018 A1 | 3/2007 | Thiagarajan | |
| 2008/0232701 A1 | 9/2008 | Gering et al. | |
| 2008/0232718 A1 | 9/2008 | Avinash et al. | |

OTHER PUBLICATIONS

Stoem et al., "Medical image compression with lossless regions of interest", Signal processing 59 (1997), 155-171.*

Poggi et al., "Pruned tree-structured vector quantization of medical images with segmentation and improved prediction", IEEE Transactions on Image Processing, vol. 4, Issue: 6, 1995, pp. 734-742.*

Krishnan, Karthik; "Efficient Transmission of Compressed Data for Remote Volume Visualization"; IEEE Transactions on Medical Imaging, vol. 25, No. 9, pp. 1189-1199; Sep. 2006.

Jia, Wenjing, et al.; "Echocardiography sequential images compression based on region of interest," ICITA 2004, 232-236.

* cited by examiner

PROCESSING OF CONTENT-BASED COMPRESSED IMAGES

BACKGROUND

The invention relates generally to the field of medical image data storage. More particularly, the invention relates to a technique for processing medical image data compressed with hierarchical data compression.

Picture archiving and communications systems, or PACS, have become an extremely important component in the management of digitized image data, particularly in the field of medical imaging. Such systems often function as central repositories of image data, receiving the data from various sources, such as medical imaging systems. The image data is stored and made available to radiologists, diagnosing and referring physicians, and other specialists via network links. Improvements in PACS have led to dramatic advances in the volumes of image data available, and have facilitated loading and transferring of voluminous data files both within institutions and between the central storage location and remote clients.

In the medical diagnostics field, depending upon the imaging modality, digitized data may be acquired and processed for a substantial number of images in a single examination, each image representing a large data set defining discrete picture elements or pixels of a reconstructed image. Computed tomography imaging systems, for example, can produce numerous separate images along an anatomy of interest in a very short examination timeframe. Ideally, all such images are stored centrally on the PACS, and made available to the radiologist for review and diagnosis.

Various techniques have been proposed and are currently in use for analyzing and compressing large data files, such as medical image data files. Image data files typically include streams of data descriptive of image characteristics, typically of intensities or other characteristics of individual pixels in the reconstructed image. In the medical diagnostic field, these image files are typically created during an image acquisition or encoding sequence, such as in an X-ray system, a magnetic resonance imaging system, a computed tomography imaging system, and so forth. The image data is then processed, such as to adjust dynamic ranges, or to enhance certain features shown in the image, for storage, transmittal and display.

While image files may be stored in raw and processed formats, many image files are quite large, and would occupy considerable disc or storage space. Moreover, an almost exponential increase in the resolutions of imaging systems has occurred and which appears will continue into the future, leading to the creation of ever larger image files, typically including more data as a result of the useful dynamic range of the imaging system, the size of the matrix of image pixels and voxels, and the number of images acquired per examination. In addition, the processing and memory requirements for current PACS systems for new clinical applications and techniques is beginning to tax current system capabilities, such as the ever increasing clinical needs for volumetric data sampled over time and for the use of multiple energy volumes for better visualization of anatomical and functional features.

In addition to occupying large segments of available memory, large image files can be difficult or time consuming to transmit from one location to another. In a typical medical imaging application, for example, a scanner or other imaging device will typically create raw data which may be at least partially processed at the scanner. The data is then transmitted to other image processing circuitry, typically including a programmed computer, where the image data is further processed and enhanced. Ultimately, the image data is stored either locally at the system, or in the PACS for later retrieval and analysis. In all of these data transmission steps, the large image data file must be accessed and transmitted from one device to another.

Current image handling techniques include compression of image data within the PACS environment to reduce the storage requirements and transmission times. Such compression techniques may, however, compress entire files, including descriptive header information which could be useful in accessing or correlating images for review. Moreover, current techniques do not offer sufficiently rapid compression and decompression of image files to satisfy increasing demands on system throughput rates and access times. Finally, alternative compression and decompression techniques do not offer the desired compression ratios, in combination with rapid compression and decompression in a client-server environment.

Another drawback of existing compression techniques is the storage, access and transmission of large data files even when a user cannot or does not desire to view the reconstructed image in all available detail. For example, in medical imaging, extremely detailed images may be acquired and stored, while a radiologist or physician who desires to view the images may not have a view port capable of displaying the image in the resolution in which they are stored. Thus, transmission of the entire images to a remote viewing station, in relatively time consuming operations, may not provide any real benefit and may slow reading or other use of the images. Furthermore, only certain portions of a medical image may be relevant for diagnosis or treatment. Thus, considerable storage space in a PACS may be allocated to the storage of medical image data that is irrelevant for the patient's diagnosis and treatment. This problem becomes even more acute as imaging systems achieve greater and greater resolutions, which correspond to a need for even more data storage space.

There is a need, therefore, for an improved image data compression and decompression technique which provides rapid compression and decompression of image files, and which obtains improved compression ratios and transmission times. In addition, there also is a need for a technique which permits compressed image data files to be created and transmitted in various resolutions or sizes, depending upon the bandwidth and desired or available resolution on a client side. Furthermore, there is a particular need for a technique to enable imaging systems to concentrate data processing resources more efficiently.

BRIEF DESCRIPTION

A technique for prioritizing portions of compressed multi-resolution medical image data to be processed is presented. More relevant, or important, portions of image data may be processed before portions of the image data that are less relevant, or important. However, the converse may also occur. The relevance of a portion of image data is based on the clinical purpose for obtaining the medical image data. The clinical purpose for obtaining the medical image is used to select a segmentation algorithm to segment the content of the image data into several regions based on their relevance to the purpose for obtaining the image data. A mask is created from the segmented data. The mask is used to assign data compression quality factors to corresponding image blocks in the image data. The image data in each region is compressed based on their assigned quality factor. The image data in regions of most relevance to the purpose for obtaining the image data may be compressed with lossless data compression. The image data in regions of lesser relevance to the purpose for obtaining the image data may be compressed with lossy data compression. The image data in the regions of most relevance, the image data in the regions of lesser relevance, and the mask are stored in long-term data storage. The image data in regions of no relevance to the purpose for obtaining the image data is discarded.

During processing, the compressed image data is accessed. In addition, the mask is accessed and used to direct the processing of the compressed image data. Depending upon the application, the mask can be used to direct that the image data for the regions of most relevance be processed before the image data for the regions of lesser relevance. However, the mask can be used to direct that the image data for the regions of lesser relevance be processed before the image data for the regions of most relevance.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
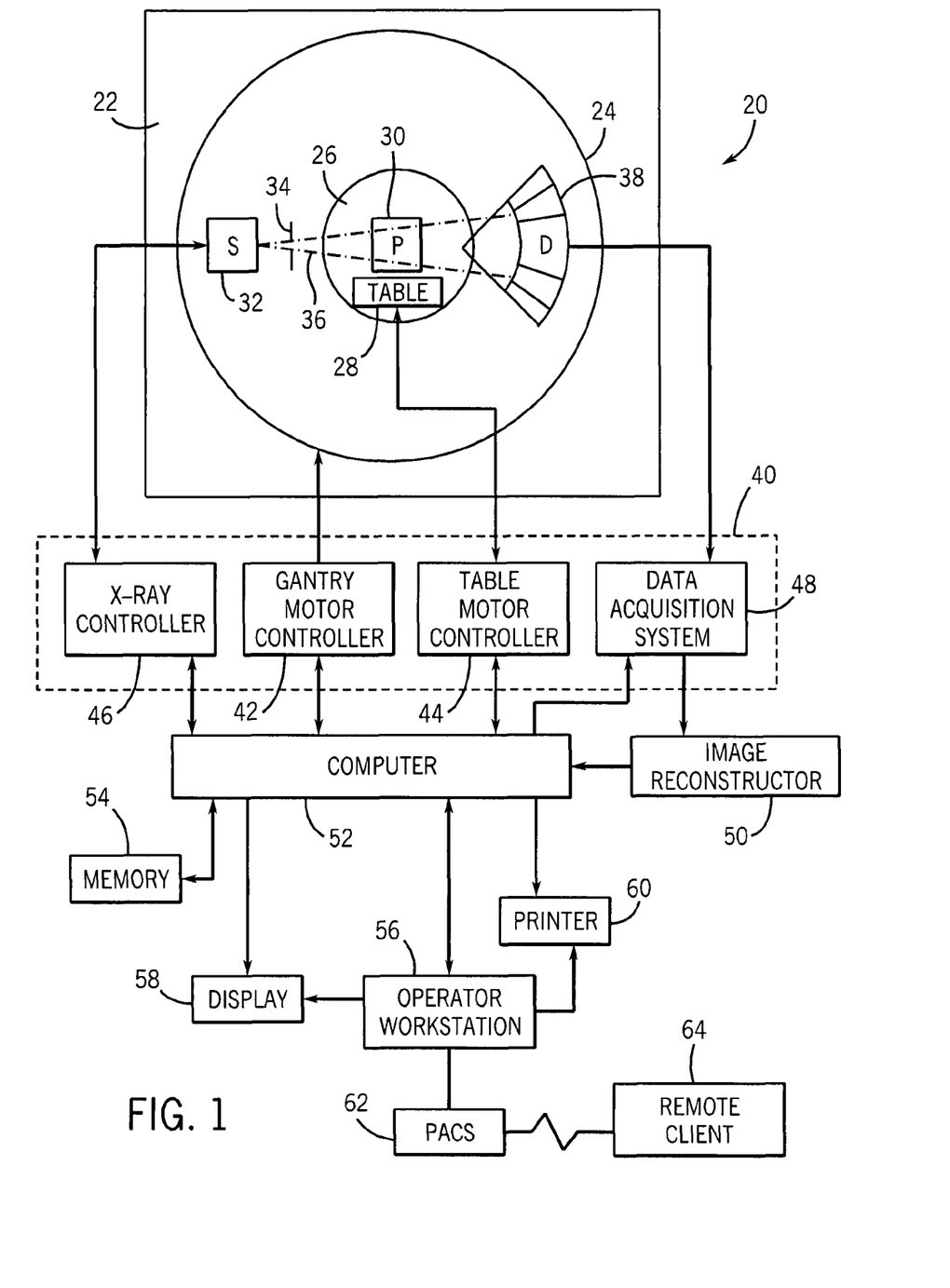
FIG. 1 is a schematic view of a Computed Tomography ("CT") imaging system, in accordance with an exemplary embodiment of the present technique.

Referring now to FIG. 1, the present invention will be described as it might be applied in conjunction with an exemplary imaging system, in this case a computed tomography (CT) imaging system. In general, however, it should be borne in mind that the present techniques may be used with image data produced by any suitable imaging modality. In a typical application, the imaging system may be designed both to acquire original image data and to process the image data for display and analysis is presented. As noted below, however, in certain applications the image data acquisition and subsequent processing (e.g., for the transformations and compression described below) may be carried out in physically separate systems or work stations. The illustrated embodiment of the CT imaging system 20 has a frame 22, a gantry 24, and an aperture (imaging volume or CT bore volume) 26. A patient table 28 is positioned in the aperture 26 of the frame 22 and the gantry 24. The patient table 28 is adapted so that a patient 30 may recline comfortably during the examination process.

The illustrated embodiment of the CT imaging system 20 has an X-ray source 32 positioned adjacent to a collimator 34 that defines the size and shape of the X-ray beam 36 that emerges from the X-ray source 32. In typical operation, the X-ray source 32 projects a stream of radiation (an X-ray beam) 36 towards a detector array 38 mounted on the opposite side of the gantry 24. All or part of the X-ray beam 36 passes through a subject, such as a patient 30, prior to impacting the detector array 38. It should be noted that all or part of the X-ray beam 36 may traverse a particular region of the patient 30, such as the liver, pancreas, heart, and so on, to allow a scan of the region to be acquired. The detector array 38 may be a single slice detector or a multi-slice detector and is generally formed by a plurality of detector elements. Each detector element produces an electrical signal that represents the intensity of the incident X-ray beam 36 at the detector element when the X-ray beam 36 strikes the detector array 38. These signals are acquired and processed to reconstruct an image of the features within the patient 30.

The gantry 24 may be rotated around the patient 30 so that a plurality of radiographic views may be collected along an imaging trajectory described by the motion of the X-ray source 32 relative to the patient 30. In particular, as the X-ray source 32 and the detector array 38 rotate along with the gantry 24, the detector array 38 collects photons resulting from X-ray beam attenuation at the various view angles relative to the patient 30 and produces signals or data representative of the incident photons. Data collected from the detector array 38 then undergoes pre-processing and filtering to condition the data to represent the line integrals of the attenuation coefficients of the scanned patient 30. The processed data, commonly called projections, are then filtered and back projected to formulate an image of the scanned area. Thus, an image or slice is acquired which may incorporate, in certain modes, less or more than 360 degrees of projection data, to formulate an image.

Rotation of the gantry 24 and operation of the X-ray source 32 are controlled by a system controller 40, which furnishes both power and control signals for CT examination sequences. Moreover, the detector array 38 is coupled to the system controller 40, which commands acquisition of the signals generated in the detector array 38. The system controller 40 may also execute various signal processing and filtration functions, such as for initial adjustment of dynamic ranges, interleaving of digital image data, and so forth. In general, system controller 40 commands operation of the imaging system 20 to execute examination protocols and to process acquired data. In the present context, system controller 40 also includes signal processing circuitry, typically based upon a general purpose or application-specific digital computer, associated memory circuitry for storing programs and routines executed by the computer, as well as configuration parameters and image data, interface circuits, and so forth. The system controller 40 includes a gantry motor controller 42 that controls the rotational speed and position of the gantry 24 and a table motor controller 44 that controls the linear displacement of the patient table 28 within the aperture 26. In this manner, the gantry motor controller 42 rotates the gantry 24, thereby rotating the X-ray source 32, collimator 34 and the detector array 38 one or multiple turns around the patient 30. Similarly, the table motor controller 44 displaces the patient table 28, and thus the patient 30, linearly within the aperture 26. Additionally, the X-ray source 32 may be controlled by an X-ray controller 46 disposed within the system controller 40. Particularly, the X-ray controller 46 may be configured to provide power and timing signals to the X-ray source 32.

In the illustrated embodiment, the system controller 40 also includes a data acquisition system 48. In this exemplary embodiment, the detector array 38 is coupled to the system controller 40, and more particularly to the data acquisition system 48. The data acquisition system 48 typically receives sampled analog signals from the detector array 38 and converts the data to digital signals for subsequent processing. An image reconstructor 50 coupled to the computer 52 may receive sampled and digitized data from the data acquisition system 48 and performs high-speed image reconstruction. Alternatively, reconstruction of the image may be done by the computer 52. Once reconstructed, the image produced by the imaging system 10 reveals internal features of the patient 30.

The data collected by the data acquisition system 48, or the reconstructed images, may be transmitted to the computer 52 and to a memory 54. It should be understood that any type of memory to store a large amount of data may be utilized by such an exemplary imaging system 10. Also the computer 52 may be configured to receive commands and scanning parameters from an operator via an operator workstation 56 typically equipped with a keyboard and other input devices. An operator may control the CT imaging system 20 via the operator workstation 56. Thus, the operator may observe the reconstructed image and other data relevant to the system from computer 52, initiate imaging, and so forth.

The CT imaging system 20 also has a display 58 that is coupled to the operator workstation 56 and the computer 52 and may be utilized by a user to observe the reconstructed image, as well as to provide an interface for control of the operation of the CT imaging system 20. In this embodiment, a printer 60 is present to enable a hard copy of a medical image to be printed. In the illustrated embodiment, the CT imaging system 20 is coupled to a picture archiving and communications system (PACS) 62 via the operator workstation 56 for long-term storage of image data. It should be noted that the PACS 62 may be coupled to a remote system 64, such as radiology department information system (RIS), hospital information system (HIS) or to an internal or external network, so that others at different locations may gain access to the image and to the image data. However, access to the image data may also be obtained remotely through the PACS 62.

It should be further noted that the computer 52 and operator workstation 56 may be coupled to other output devices, such as a standard or special purpose computer monitor and associated processing circuitry. One or more operator workstations 56 may be further linked in the CT imaging system 20 for outputting system parameters, requesting examinations, viewing images, and so forth. In general, displays, printers, workstations, and similar devices supplied within the CT imaging system 20 may be local to the data acquisition components, or may be remote from these components, such as elsewhere within an institution or hospital, or in an entirely different location, linked to the imaging system CT via one or more configurable networks, such as the Internet, virtual private networks, and so forth.

As noted above, it should be borne in mind that the CT system referred to herein is merely one exemplary source of image data that may be handled in accordance with the present techniques. Most such systems will include operator interfaces and software specifically adapted to acquire image data and to at least partially process the data in accordance with the specific physics of the imaging modality. Indeed, other arrangements of CT systems, other reconstruction techniques, and so forth may give rise to image data that may be managed as described herein.

Figure 2:
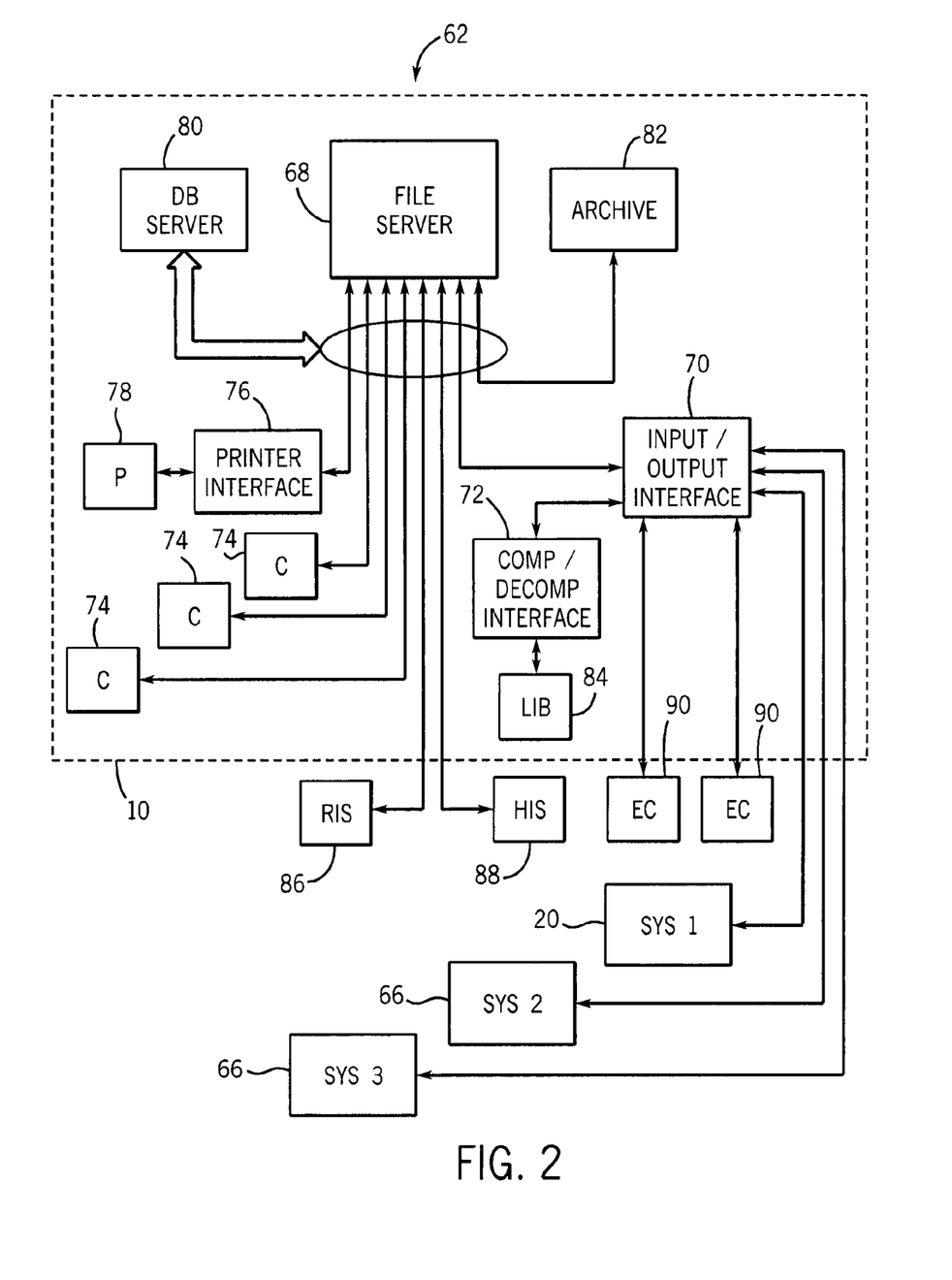
FIG. 2 is a diagrammatical representation of a picture archiving and communication system, or PACS, for receiving and storing image data from the CT imaging system of FIG. 1, in accordance with an exemplary embodiment of the present technique.

Referring generally to FIG. 2, an exemplary embodiment of a PACS 62 for receiving, compressing and decompressing image data is presented. In the illustrated embodiment, the CT imaging system 20 is used for short-term storage of image data only. Memory 54 of the CT imaging system 20 is limited and cannot be used to store image data with any degree of permanence, particularly when the system is used to carry out examinations for a large number of patients in a clinic, hospital or other institution. For example, data space occupied by old image data may be written over by new image data. The PACS 62 is used for long-term storage of medical image data. In the illustrated embodiment, PACS 62 receives image data from CT imaging system 20, as well as several other separate imaging systems designated by reference numeral 66. As will be appreciated by those skilled in the art, the imaging systems may be of various type and modality, such as MRI systems, PET systems, radio fluoroscopy (RF), computed radiography (CR), ultrasound systems, digital X-ray systems, X-ray tomosynthesis systems, ultrasound systems, and so forth. Moreover, the systems may include processing stations or digitizing stations, such as equipment designed to provide digitized image data based upon existing film or hard copy images. It should also be noted that the systems supplying the image data to the PACS may be located locally with respect to the PACS, such as in the same institution or facility, or may be entirely remote from the PACS, such as in an outlying clinic or affiliated institution. In the latter case, the image data may be transmitted via any suitable network link, including open networks, proprietary networks, virtual private networks, and so forth.

PACS 62 includes one or more file servers 68 designed to receive and process image data, and to make the image data available for decompression and review. File server 68 receives the image data through an input/output interface 70. Image data may be compressed in routines accessed through a compression/decompression interface 72. As described more fully below, compression/decompression interface 72 serves to compress the incoming image data rapidly and optimally, while maintaining descriptive image data available for reference by file server 68 and other components of the PACS. Where desired, compression/decompression interface 72 may also serve to decompress image data accessed through the file server 68. The file server 68 is also coupled to internal clients, as indicated at reference numeral 74, each client typically including a work station at which a radiologist, physician, or clinician may access image data from the server, decompress the image data, and view or output the image data as desired. Clients 74 may also input information, such as dictation of a radiologist following review of examination sequences. Similarly, file server 68 may be coupled to one or more interfaces, such as a printer interface 76 designed to access and decompress image data, and to output hard copy images via a printer 78 or other peripheral.

A database server 80 is used to associate image data, and other work flow information within the PACS, by reference to one or more file servers 68. In the presently contemplated embodiment, database server 80 may include cross-referenced information regarding specific image sequences, referring or diagnosing physician information, patient information, background information, work list cross-references, and so forth. The information within database server 80 serves to facilitate storage and association of the image data files with one another, and to allow requesting clients to rapidly and accurately access image data files stored within the system. Similarly, file server 68 is coupled to one or more archives 82, such as an optical storage system, which serve as repositories of large volumes of image data for backup and archiving purposes. Techniques for transferring image data between file server 68, and any memory associated with file server 68 forming a short-term storage system, and archive 82, may follow any suitable data management scheme, such as to archive image data following review and dictation by a radiologist, or after a sufficient time has lapsed since the receipt or review of the image files.

In the illustrated embodiment, other components of the PACS system or institution may be integrated with the foregoing components to further enhance the system functionality. For example, a compression/decompression library 84 is coupled to compression/decompression interface 72 and serves to store compression routines, algorithms, look up tables, and so forth, for access by input/output interface 70 (or other system components) upon execution of compression and decompression routines (i.e. to store various routines, software versions, code tables, and so forth). In practice, compression/decompression interface 72 may be part of compression/decompression library 84. Library 84 may also be coupled to other components of the system, such as internal clients 74 or printer interface 76, serving similarly as a library or store for the compression and decompression routines and algorithms. Although illustrated as a separate component, it should be understood that compression/decompression library 84 may be included in any suitable server or memory device, including within file server 68. Moreover, code defining the compression and decompression processes described below may be loaded directly into compression/decompression interface 72 and/or compression/decompression library 84, or may be loaded or updated via network links, including wide area networks, open networks, and so forth.

Additional systems may be linked to the PACS, such as directly to server 80, or through interfaces such as input/output interface 70. In the embodiment illustrated in FIG. 2, a radiology department information system or RIS 86 is linked to file server 68 to facilitate exchanges of data, typically cross-referencing data within database server 80, and a central or departmental information system or database. Similarly, a hospital information system or HIS 88 may be coupled to database server 80 to similarly exchange database information, workflow information, and so forth. Where desired, such systems may be interfaced through data exchange software, or may be partially or fully integrated with the PACS system to provide access to data between the PACS database and radiology department or hospital databases, or to provide a single cross-referencing database. Similarly, external clients, as designated at reference numeral 90, may be interfaced with the PACS to enable images to be viewed at remote locations. Such external clients may employ decompression software, or may receive image files already decompressed by compression/decompression interface 72. Again, links to such external clients may be made through any suitable connection, such as wide area networks, virtual private networks, and so forth.

In the illustrated embodiment, the PACS 62 provides for multi-resolution (or multi-size) image data compression. Where a user does not desire to view a full image with maximum resolution, or where the user view port is limited, such multi-resolution image compression facilitates transfer of a reduced size image to the user for viewing, with excellent image quality. Moreover, the multi-resolution image compression may allow a user to view a reduced size or reduced resolution image relatively rapidly, and to "zoom" on the image thereafter by transfer of only a portion of the compressed data corresponding to components of the greater sized image not already transferred. The additional data is then processed and combined with the reduced size image data to obtain the larger sized image. In addition, the technique described below utilizes purpose-driven image data storage to reduce the amount of stored image data associated with an image stored in the PACS 62.

It should be noted that the processing and storage of the image data as described below may be performed in the PACS 62, or in any other suitable system component or components. The processing will typically be embodied in computer code that can be stored and executed on any one or more than one of the computers of the acquisition the PACS, an operator workstation, server, and so forth, so long as the system is capable of performing the computations involved.

The multi-resolution implementation may be based partially upon lossless integer wavelet decomposition. Specifically, as will be recognized by those skilled in the art, wavelet decomposition involves a dyadic filtering and sub-sampling process. This creates a hierarchical set of sub-bands. As will be discussed in more detail below, a wavelet transformed image data set includes low frequency components along with high frequency components, which may be considered as noise or variations from the low frequency components. A single level wavelet decomposition results in a decomposed data set which includes one low frequency sub-band LL, along with three high frequency ones LH, HL, and HH. Subsequent decomposition may be considered to produce a further data set in which the low frequency sub-band is further decomposed into a set of sub-bands, including a low frequency band, along with three additional high frequency sub-bands.

Figure 3:
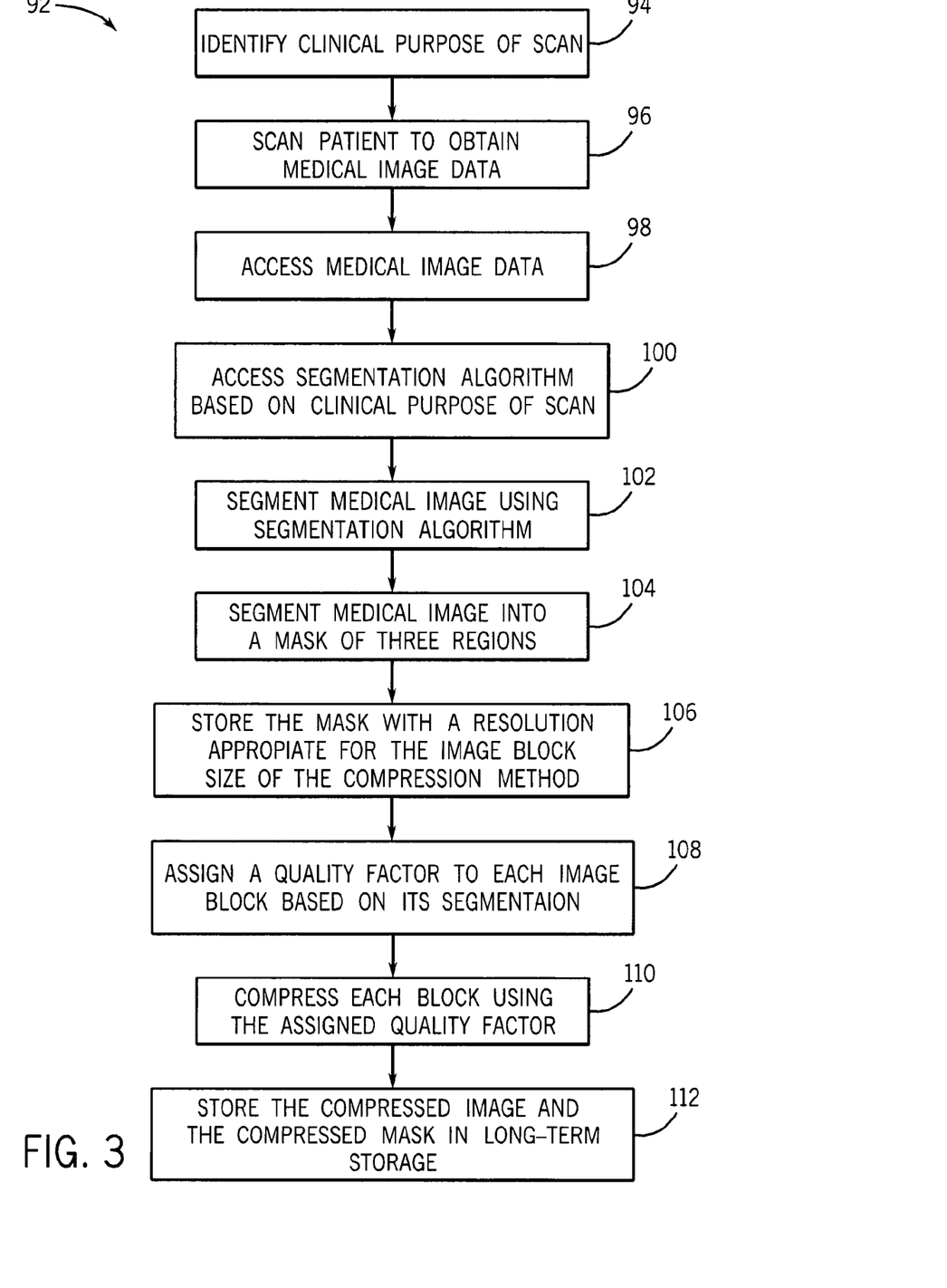
FIG. 3 is a block diagram of an exemplary technique for selectively storing medical image data based on the content of the image, in accordance with an exemplary embodiment of the present invention.

Referring generally to FIG. 3, a technique is presented for selectively storing image data within an image based on the content of the image, represented generally by reference numeral 92. The illustrated technique enables the amount of medical image data that is stored in the PACS 62 for each medical image taken to be reduced. By knowing the purpose for obtaining the medical image data, it is possible to identify the content of the medical image that is highly relevant and the content of the medical image that is of lesser relevance, or even irrelevant. In the illustrated embodiment, the content of the medical image that is highly relevant is compressed with lossless data compression, which maintains its full resolution. The content of the medical image that is less relevant is compressed with lossy data compression, which results in a lower resolution for those regions of the image. The content of the medical image that is not relevant is discarded completely. After data compression, the contents of the image that are either highly relevant or of a lesser relevance are stored in long-term storage in the PACS 62. Because not all of the image data for an image is stored at full resolution, the amount of data storage space required by the image is reduced.

As will be discussed in more detail below, the different contents of the medical image are assigned a quality factor that establishes the relevance, and, therefore, the type of data compression at which that portion of the image data will be compressed, or whether it will be compressed at all in the case of irrelevant image data. In this embodiment, any portion of medical image data that is assigned a quality factor corresponding to highly relevant image data is compressed with lossless compression. Any portion of medical image data that is assigned a quality factor that corresponds to less relevant image data is compressed with lossy compression and stored with less than full resolution. Finally, any portion of medical image data that is assigned a quality factor that corresponds to irrelevant image data is discarded and not compressed, at all.

The compression quality factor that a particular region or anatomical feature is assigned is based on the clinical purpose for obtaining the medical image data. Depending on the clinical purpose of the scan, an anatomical feature may be of great interest in one medical image and of little or no interest in another medical image. For example, if the purpose of the scan is to enable a radiologist to look for tumors in the brain, anatomical features other than the brain would be of lesser interest. Therefore, in this example, brain tissue image data is highly relevant and would have a quality factor assigned to it to reflect that it is highly relevant. On the other hand, blood vessel image data is of a lesser relevance and would be assigned a quality factor to reflect its lesser relevance. Similarly, cerebrospinal fluid is irrelevant and would have a quality factor assigned to it to reflect its irrelevance.

The technique calls for identifying the clinical purpose for obtaining the medical image data, as represented generally by block 94. There may be any of a myriad of clinical purposes for obtaining the medical image data, such as an angiogram, a mammogram, a perfusion, to locate a tumor, an aneurysm, blocked blood vessels, etc. In addition, the scan may be performed for any portion of the body. A system operator may select the purpose from a menu or list or purposes, thereby directing the system to automatically execute the steps of the technique.

To obtain medical image data the patient is scanned using the CT imaging system 20, represented generally by block 96. In the illustrated embodiment, the image data that is obtained is three-dimensional image data. However, additional dimensions of image data corresponding to various other types of data, such as time, temperature, pressure, etc., may be obtained, as well. In the illustrated embodiment, the medical image data that is obtained by scanning the patient is obtained at a single resolution, which is the highest resolution available from the CT imaging system 20. As noted above, this technique is applicable for use with imaging systems other than the CT imaging system 20. For imaging technologies based upon other physical parameters, the intensity, color, brightness or another parameter or characteristic of each pixel or voxel will be based the unique physics of that technology (e.g., net magnetic moment for MRI systems, gamma radiation received for PET imagines systems, and so forth).

The full resolution medical image data is then accessed for further processing before long-term storage, represented generally by block 98. The medical image data may be processed by the CT imaging system 20 and/or the PACS 62. However, in this embodiment, the CT imaging system 20 is not used for long-term storage of medical image data. Instead, long-term storage of medical image data occurs in the PACS 62. However, in other embodiments of the present technique, an imaging system may be used for long-term storage of medical image data, rather than a PACS.

A segmentation algorithm is selected to segment the contents of the medical image data based on the clinical purpose of the scan, as represented by block 100. For example, if the purpose of the scan is to enable a radiologist to examine the brain for tumors, a segmentation algorithm could be selected that is adapted to segment the various tissues of the head, such as brain tissue, bone, skin, etc. As another example, if the purpose of the scan was to examine the condition of the cartilages of the knee, a segmentation algorithm could be selected that is adapted to segment cartilage from other tissues, such as bone, muscle, and ligaments. A copy of the original image data may be used for segmentation purposes. Once selected, the segmentation algorithm is then used to segment the image data, represented generally by block 102. In the illustrated embodiment, the segmented image data is three-dimensional image data.

In the illustrated embodiment, the segmented image data is used to create a mask having at least three groups based on their relevance to the clinical purpose for obtaining the image data, represented generally by block 104. In this embodiment, the segmentation algorithm is operable to classify the segmented portions of the image data into three groups based on their relevance to the clinical purpose for obtaining the medical image data. The three groups are image data having highly relevant content, image data having less relevant content, and image data having no relevant content. For example, a segmentation algorithm may segment brain tissue, bone, and ventricles filled with cerebrospinal fluid within an image of the brain. In this embodiment, in addition to segmenting the portions of the image data, the segmentation program would also establish the degrees of relevance for the brain tissue, bone, and ventricles filled with cerebrospinal fluid based on the clinical purpose for obtaining the medical image data. If the purpose for obtaining the image data is for identifying brain tumors, the brain tissue would be identified as highly relevant and the bone would be identified as less relevant, or perhaps irrelevant. Similarly, the ventricles filled with cerebrospinal fluid would be identified as irrelevant. If there were another purpose for obtaining the image data, the degrees of relevance for the various tissues might change. The mask comprises three-dimensional image data in this embodiment. In addition, instead of the segmentation algorithm, a separate algorithm may be used to create the mask in another embodiment.

The mask is comprised of image blocks that are assigned quality factors that correspond to the three groups of image data. A different quality factor is assigned to each group of image data to distinguish them. For example, an image block in the mask that corresponds to highly relevant image data may be assigned with a quality factor of "two." Similarly, each portion of the mask that corresponds to less relevant image data may be assigned with a quality factor of "one" and an image block in the mask that corresponds to irrelevant image data may be assigned a quality factor of "zero." However, these numbers are arbitrary and may vary depending upon the system in which the technique is utilized. The mask is stored with a resolution appropriate for the image block size of the compression, as represented generally by block 106.

A quality factor is then assigned to each image block in the image data based on the quality factors assigned to the mask, represented generally by block 108. The quality factors of the image blocks of the mask are transferred to the corresponding image blocks in the image data. In the example described above, all image blocks of the highly relevant image data are assigned a quality factor of "two", the image blocks of the less relevant image blocks are assigned a quality factor of "one", and the image blocks of the irrelevant image data are assigned a quality factor of "zero".

The medical image data is then compressed using the assigned quality factors, represented generally by block 110. Using the quality factors, the image blocks corresponding to the highly relevant image data are compressed losslessly. Image blocks corresponding to the less relevant image data are compressed with lossy compression. Finally, image blocks corresponding to the irrelevant image data are discarded and not compressed. In the illustrated embodiment, the PACS 62 compresses the image data. The PACS identifies the quality factor for each image block prior to data compression and then uses the appropriate algorithm or tool to compress the block of image data. The image data may also be decomposed into a plurality of resolution levels using wavelet transformation.

After data compression, the compressed image and the compressed mask are stored in long-term storage, represented generally by block 112. From there, the image data may be retrieved from long-term storage for viewing at any time. Because not all of the image data was stored with lossless compression, the amount of data storage space needed to store each image is reduced. However, because all of the highly relevant image data is saved with lossless data compression, there is no loss of image data or resolution in the highly relevant regions of the image. In addition, the less relevant image data is provided for clarity, but at a lower resolution that the highly relevant image data. The resolution of the less relevant image data may be set to a desired value.

Figure 4:
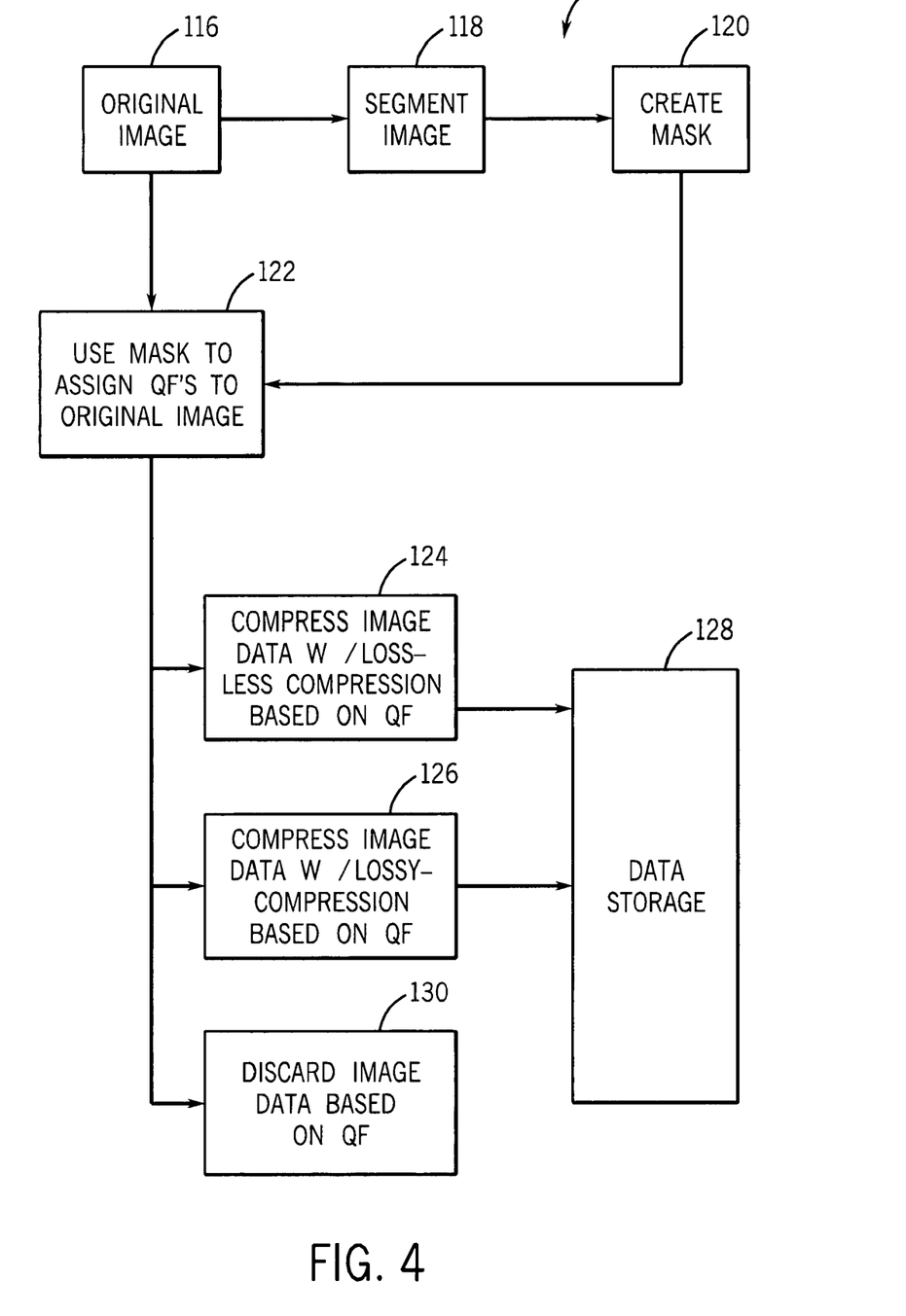
FIG. 4 is a diagrammatical representation of the technique of FIG. 3, in accordance with an exemplary embodiment of the present invention.

Referring generally to FIG. 4, a diagrammatical representation of the technique for selectively storing image data based on the content of the image is presented, referenced generally by reference numeral 114. An original image 116 is used to create a segmented image 118. As also noted above, a segmentation algorithm is used to segment the original image based on the clinical purpose for the exam. The segmented image 118 is then used to create a mask 120. The mask 120 is then used to assign different quality factors to various regions of the original image 122, as represented by block 122. The various portions of the image data are then processed based on their assigned quality factors, represented by block 124. Those portions of the image data having highly relevant or less relevant values are compressed according to their assigned quality factor, represented by block 126. As noted above, those portions of the image data having highly relevant status are compressed with lossless resolution, while those portions having less relevant status are compressed with lossy compression at less than full resolution. The compressed data is then stored in long-term storage, as represented by block 126. Those portions of the image data having quality factors corresponding to irrelevant image data are discarded and not stored in long-term storage, represented by block 130. Thus, images that are stored in long-term storage will not have any image data for the discarded regions. As a result, images produced from the image data stored in long-term storage are composed of portions, or regions, having different resolutions. The most relevant portions of the image have full resolution, while images with less relevance have lower resolutions. In addition, the image may be decomposed using wavelet decomposition to produce different levels of image resolution. Each resolution level in such a multi-resolution image set would have a full resolution portion (for that resolution level) and a lower resolution portion (for that resolution level).

Figure 5:
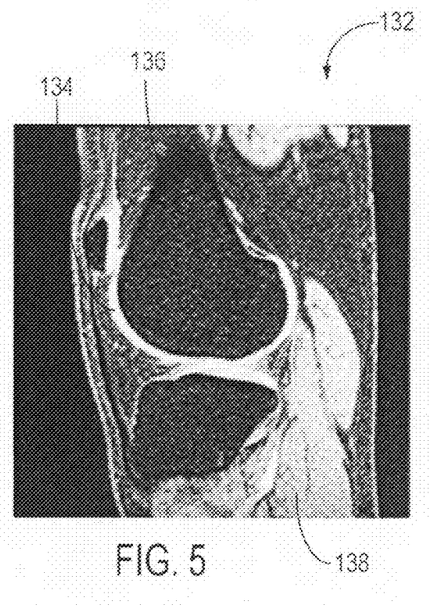
FIG. 5 is an exemplary medical image taken along the saggittal plane of the knee, in accordance with an exemplary embodiment of the present invention.

Referring generally to FIG. 5, a reconstructed image slice of a patient's knee is presented, referenced generally by reference numeral 132. In this image, the clinical purpose for obtaining the image data is to examine the condition of the femoral cartilage 134 within the knee 132. In addition to the femoral cartilage 134, various bones 136 of the knee 134, including portions of the femur and tibia, are shown. In addition, other soft tissues 138 are shown, such as muscles and ligaments.

Figure 6:
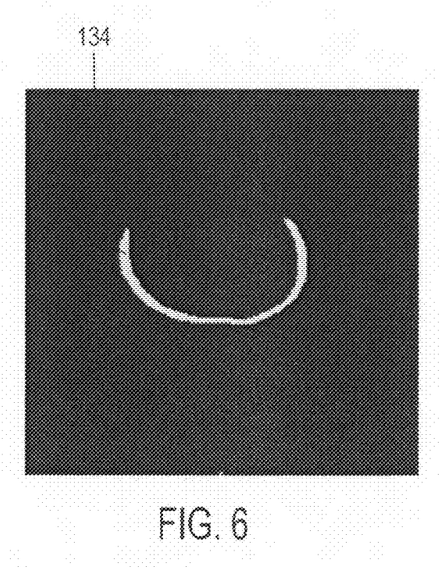
FIG. 6 is an exemplary segmented image data from FIG. 5, in accordance with an exemplary embodiment of the present invention.

Referring generally to FIG. 6, a segmented image of the femoral cartilage 134 is presented. In addition, other tissues of the knee are segmented and used to form the mask.

Figure 7:
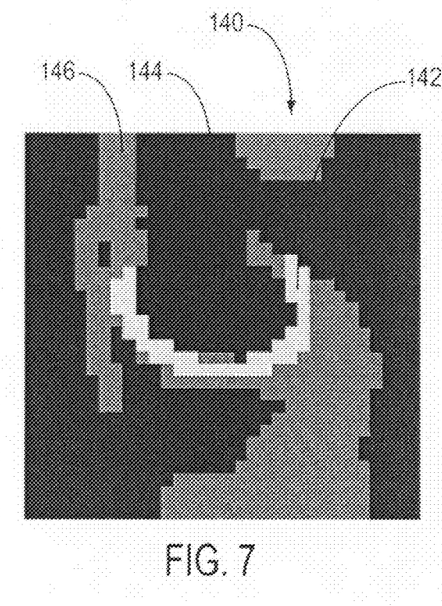
FIG. 7 is an image mask created from segmented image of FIG. 5, in accordance with an exemplary embodiment of the present invention.

Referring generally to FIG. 7, a mask, represented generally by reference numeral 140, of the knee of FIG. 5 is presented. In this embodiment, the mask 140 has three regions representing the three groups of tissues, each region having its own quality factors. The image blocks 142 corresponding to the femoral cartilage are assigned a quality factor to signify that these image blocks have the most relevance. In this particular embodiment, the image blocks 142 corresponding to the femoral cartilage are the most relevant and have an assigned quality factor of "two". The image blocks 144 corresponding to the bones of the knee are irrelevant and are assigned a quality factor of "zero" to signify that these image blocks are irrelevant. Finally, the image blocks 146 corresponding to the soft tissues of the knee are assigned a quality factor of "one" to signify that these image blocks are relevant, but less relevant than the femoral cartilage.

As discussed above, the mask 140 is used to assign quality factors to the knee 132 of FIG. 5 to direct the compression of the image data. In this embodiment, those portions of the image of the knee 132 that are assigned the quality factor having a value of "two" are compressed with lossless compression. In this example, that corresponds to the femoral cartilage and some of its adjacent tissue. Other portions of the knee 132 that are assigned quality factors having a value of "one" are compressed with lossy compression. In this example, that corresponds to the soft tissues 138 of the knee 138. As a result, the soft tissues have a lower resolution than the femoral cartilage 134 when viewed after the data has been compressed. Finally, the portions of the knee 132 that are assigned a quality factor of "zero" are simply discarded and not stored in long-term storage. In this example, that corresponds to bone. As a result, less data storage space is required to store the image than if all of the regions of the image had been stored at full resolution. However intended are presented in full resolution. In this example, that is the femoral cartilage and some adjacent tissue.

Figure 8:
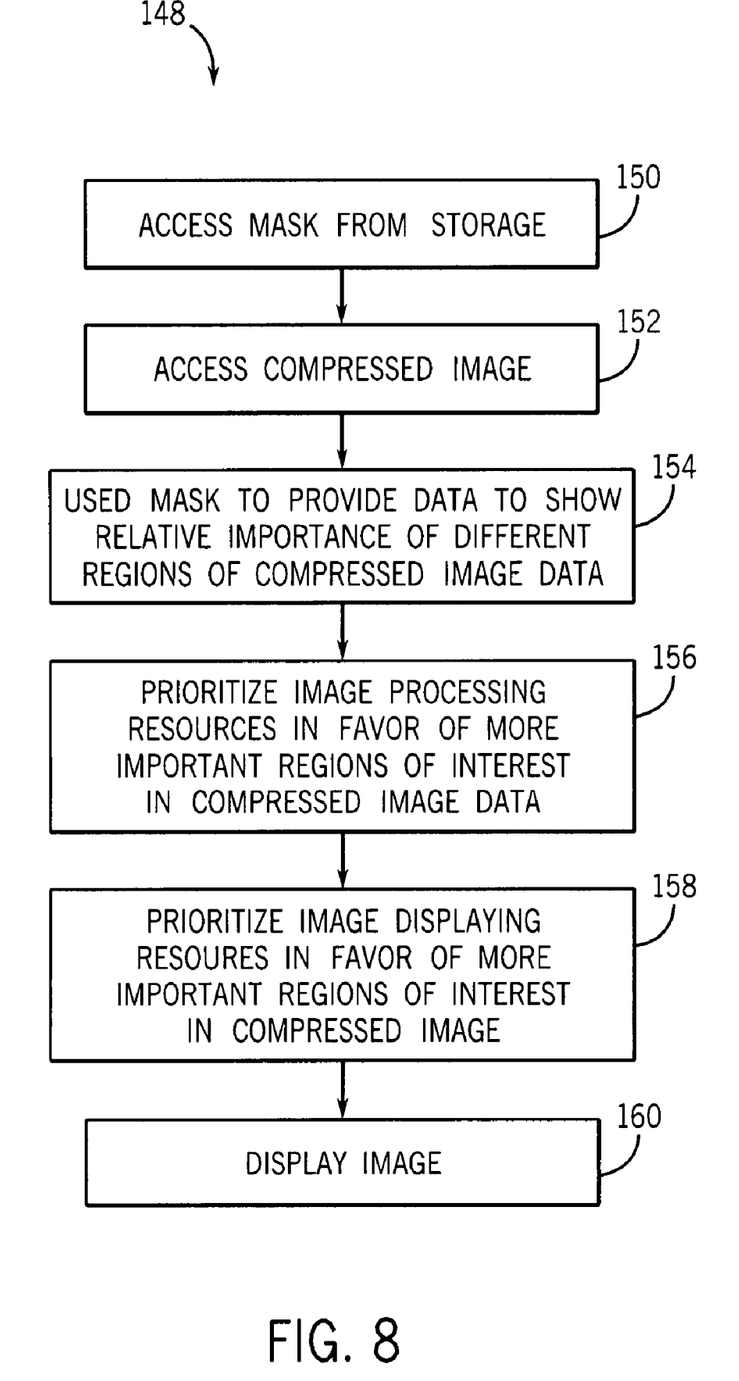
FIG. 8 is a block diagram of an exemplary technique for selectively processing medical image data having regions of the image data compressed with different degrees of data compression based on the content of the image, in accordance with an exemplary embodiment of the present invention.

Referring generally to FIG. 8, a technique for processing image data compressed using the technique described above is presented, and referenced generally by reference numeral 148. The mask provides a map of the image data to distinguish highly relevant regions of the image data from regions of lesser relevance or irrelevance. The mask also enables the processing of the compressed image data to be differentiated among the regions of the image data based on the relevance of the region. In the illustrated embodiment, at least one level of the multi-resolution image data is adaptively processed based on the relevancy information stored in the mask. The adaptive processing may take several forms. For example, more relevant/important regions of image data may be processed before less relevant regions of image data.

The mask is accessed from long-term storage in this embodiment, represented generally by block 150. In addition, the compressed image data is accessed from long-term data storage, represented generally by block 152. The mask may be used to establish the portion of compressed image data to access. In the illustrated embodiment, the mask is used to provide data on the relative importance of the different regions of interest in the compressed image data, represented by block 154.

In the illustrated technique, image processing resources are prioritized based on the relevancy data provided by the mask, represented generally by block 156. For example, the mask can be used to direct the segmentation or registration of the image data. Segmentation of the image data by relevance may be accomplished easily using the relevance data in the mask, e.g., the mask may be used as guidance so that only high relevance image data is retrieved from storage, decompressed, and processed. The mask can serve as a guide for other types of segmentation, as well. Registration and segmentation techniques often use stochastic sampling of the image gradients to save time and processing resources. By using the mask, the random samples from the image regions can be directed to the regions of highest relevance or importance. However, in other applications, the regions of lesser relevance may be processed before the regions of more relevance. Other examples of using the relevancy data to guide image processing are provided below.

In the alternative to or in addition to prioritizing the image processing resources, image display resources are prioritized based on the data provided by the mask, represented generally by block 158. For example, more relative/important regions of image data may be processed for display before less relevant regions of image data. The processed image data is then displayed for viewing on a monitor or other viewing device, represented generally by block 160.

Figure 9:
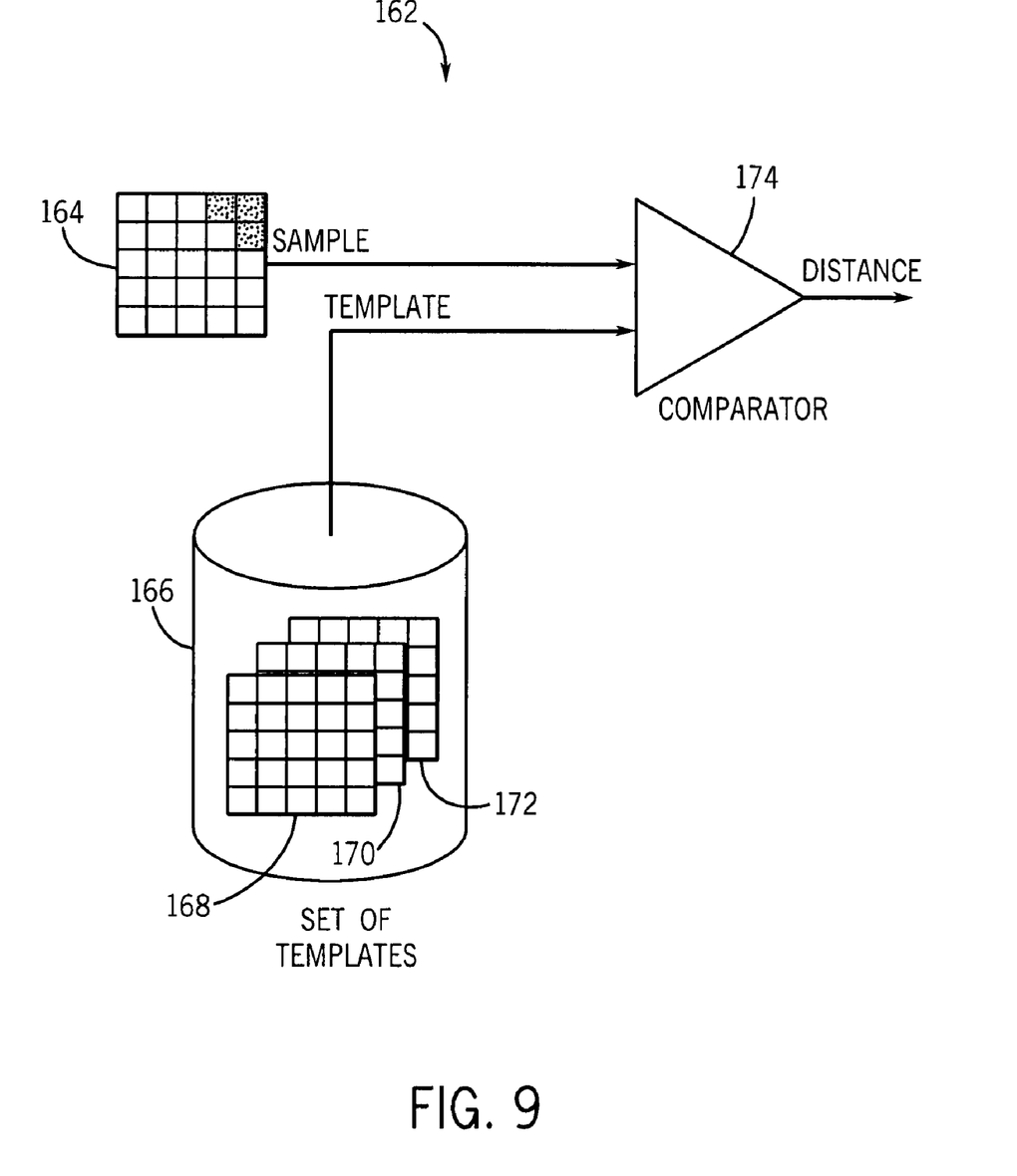
FIG. 9 is a diagrammatical representation of a technique for selectively processing compressed medical image data having regions of the image data compressed with different degrees of data compression based on the content of the image, in accordance with an exemplary embodiment of the present invention.

Referring generally to FIG. 9, an example of a computer-assisted diagnosis (CAD) technique using pattern-matching is presented, and represented generally by reference numeral 162. The CAD technique is another example of using the relevancy data to guide image processing. The illustrated embodiment of a CAD technique benefits from the use of a multi-resolution imaging and the mask to prioritize the pattern-matching process on more relevant regions of image data. Regions of a stored image 164 are compared to templates within a set of templates 166. In the illustrated embodiment, the set of templates 166 is comprised of a first template 168, a second template 170, and a third template 172. However, the set of templates 166 may be comprised of many more templates. The set of templates 166 are representative of a relevant region, such as a lesion.

A comparator algorithm 174 is used to perform a comparison for pattern-matching. The lower resolution versions of the multi-resolution image data are used initially to compare with a similar resolution template. The best matches from the initial comparison are further analyzed using higher resolution versions of the multi-resolution image data. The mask is used to direct the matching process to use the more relevant regions of the image data for comparison. The mask can also be used to direct the pattern matching process to use finer processing in the more relevant regions of the image data.

In another embodiment of the present technique, the relevancy data is used to guide image processing for content-based image retrieval (CBIR). CBIR techniques also uses pattern-matching to search an image database for stored images that best match a sample image provided for the search. As above, the lower resolution versions of the multi-resolution image data are used initially for comparison with the sample image. The best matches from the initial comparison are further analyzed using higher resolution versions of the multi-resolution image data. The mask is used to direct the matching process to use the more relevant regions of the image data for comparison. As above, the mask can also be used to direct the pattern matching process to use finer processing in the more relevant/important regions of the images in the image database.

Figure 10:
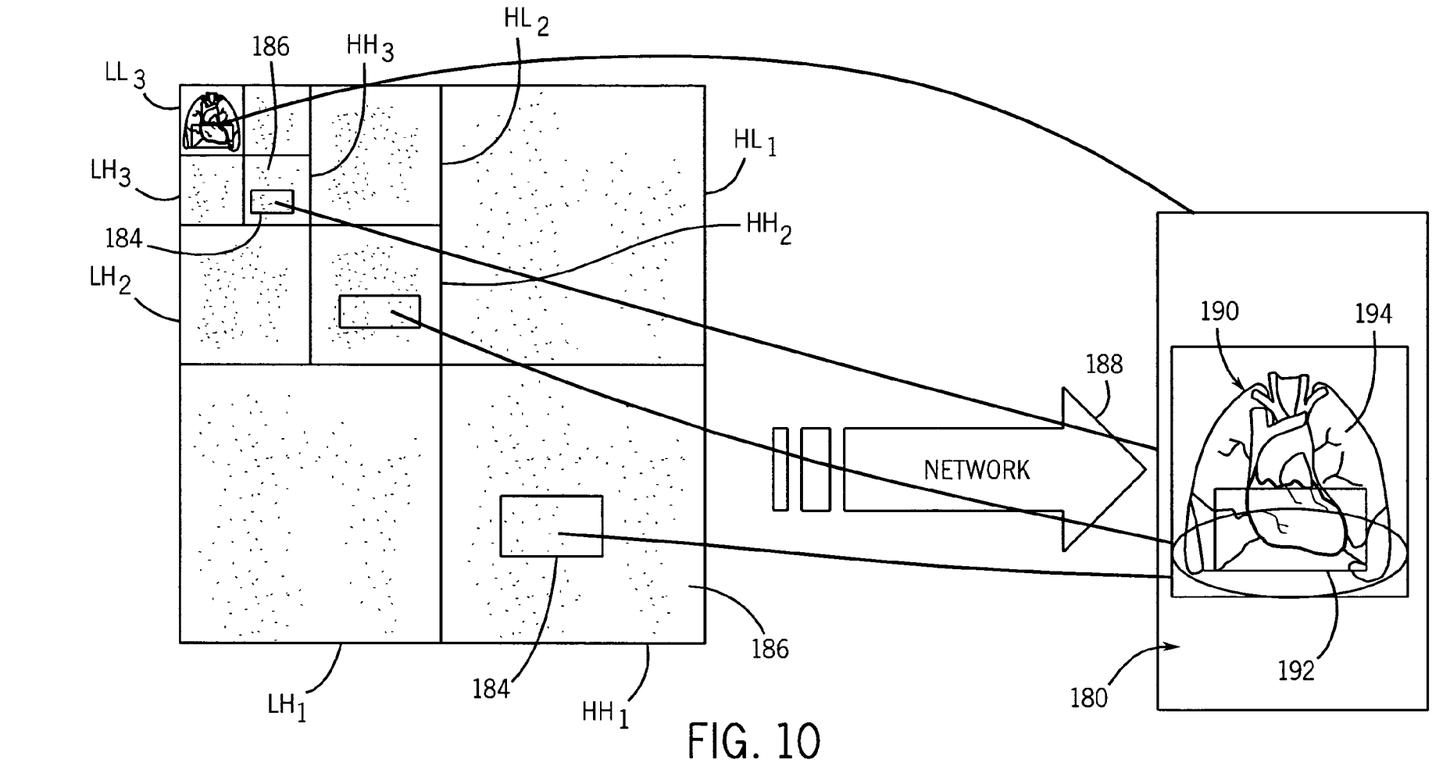
FIG. 10 is a diagrammatical representation of a technique for selectively processing compressed medical image data having regions of the image data compressed with different degrees of data compression based on the content of the image, in accordance with an exemplary embodiment of the present invention.

Referring generally to FIG. 10, an example of an image displaying technique that utilizes a mask to prioritize image data from more relevant regions of multi-resolution image data is presented, and represented generally by reference numeral 176. In the illustrated embodiment, multi-resolution image data and a multi-resolution mask are stored in a PACS. However, the image data may be stored in another form of data storage. The multi-resolution image data, represented generally by reference numeral 178, is processed by the PACS and transmitted to a hand-held image displaying device 180 having a display 182.

The multi-resolution implementation of the image data creates a hierarchical set of sub-bands. The multi-resolution image data 178 includes low frequency components along with high frequency components, which may be considered as noise or variations from the low frequency components. A single level wavelet decomposition results in a decomposed data set which includes one low frequency sub-band LL, along with three high frequency ones LH, HL, and HH. Subsequent decomposition may be considered to produce a further data set in which the low frequency sub-band is further decomposed into a set of sub-bands, including a low frequency band, along with three additional high frequency sub-bands. In the illustrated embodiment, there are three levels of image resolution, each represented by a subscript 1, 2, or 3. The low frequency sub-band of the first resolution level is decomposed to produce the second resolution level. The low frequency sub-band of the second resolution level is decomposed to produce the third resolution level.

As discussed above, different regions of the image data are compressed with different data compression based on the content of the image as defined by the purpose for obtaining the image. Regions of image data that are highly relevant are compressed with lossless compression, regions of image data with lesser relevance are compressed with lossy compression and regions of image data that are not relevant are discarded. Thus, each resolution level and each sub-band may have regions having different resolutions. In the illustrated embodiment, the low frequency sub-band of the third resolution level, $LL_3$, is used to provide a low resolution overview of the entire image. In the illustrated embodiment, the high frequency sub-bands at each resolution level have a region of high relevance that was compressed with lossless compression, represented generally by reference numeral 184, and a region of lesser relevance that was compressed with lossy compression, represented generally by reference numeral 186. For clarity, the regions of high relevance in the high frequency sub-bands are shown only in the HH sub-band of each resolution level. However, these regions are present in the LH and HL sub-bands, as well. No regions having image data that has been discarded prior to data compression are shown in the illustrated embodiment. However, in other embodiments the sub-bands may have regions where image data has been discarded prior to data compression.

In the illustrated embodiment, the multi-resolution image data 178 is transmitted to the hand-held image displaying device 180 via a wireless network 188. However, the technique is applicable with other types of devices and other types of networks. In the illustrated embodiment, a mask is used to direct the PACS to transmit the regions of high relevance 184 in the high frequency sub-bands before the regions of lesser relevance 186. The low frequency sub-band in the third resolution level, $LL_3$, may be transmitted before, during, or after the regions of high relevance 184 in the high frequency sub-bands are transmitted. The mask may also be used to initialize the hand-held imaging device 180 based on the relevance of the different regions of the image. Initialization of the hand-held imaging device 180 includes setting the zoom, pan, and window levels.

In the illustrated embodiment, a complete image 190 is displayed on the display 182 of the hand-held image displaying device 180. The image 190 has a higher resolution portion 192 corresponding to the most relevant regions of the image data and a lower resolution portion 194 corresponding to the regions of lesser relevance.

Alternatively, multiple masks may be created to enable sub-regions of regions of importance to be differentiated during subsequent processing. These multiple masks may also be saved in long-term storage so that they may be available for image data processing at a later time.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method for processing image data, comprising:
    accessing compressed image data comprising a plurality of resolution levels of compressed image data, wherein at least one resolution level of compressed image data comprises a first region of algorithmically segmented image data along contours of a specific tissue of interest compressed with lossless compression and a second region of algorithmically segmented image data along the contours of the specific tissue of interest compressed with lossy compression;
    accessing a mask, wherein a first region of the mask corresponding to the first region of algorithmically segmented image data is labeled with a first identifier, a second region of the mask corresponding to the second region of algorithmically segmented image data is labeled with a second identifier, and a third region of the mask corresponding to discarded image data is labeled with a third identifier; and
    selectively processing the first region and the second region of the segmented image data based on the first and second identifiers in the mask.

2. The computer-implemented method for processing image data as recited in claim 1, wherein selectively processing the first region and the second region of the algorithmically segmented image data comprises modifying a parameter of a processing algorithm based on the first and second identifiers in the mask.

3. The computer-implemented method for processing image data as recited in claim 1, wherein selectively processing the first region and the second region of the algorithmically segmented image data based on the first and second identifiers in the mask comprises processing the first region of segmented image data before processing the second region of segmented image data.

4. The computer-implemented method for processing image data as recited in claim 3, wherein the first region of algorithmically segmented image data has a greater resolution than the second region of algorithmically segmented image data.

5. The computer-implemented method for processing image data as recited in claim 1, wherein accessing compressed image data comprises decompressing the at least one resolution level of compressed image data.

6. The computer-implemented method for processing image data as recited in claim 5, wherein the mask comprises a plurality of resolution levels of compressed mask data and accessing a mask comprises decompressing compressed mask data having a resolution level corresponding to the at least one resolution level of compressed image data.

7. The computer-implemented method for processing image data as recited in claim 1, wherein accessing compressed image data and accessing a mask comprises accessing the compressed image data and the mask from long-term data storage.

8. The computer-implemented method for processing image data as recited in claim 1, wherein the compressed image data and the mask comprise three-dimensional image data.

9. The computer-implemented method for processing image data as recited in claim 1, wherein the first and second identifiers comprise a plurality of compression quality factors, a first compression quality factor corresponding to the first identifier and a second compression quality factor corresponding to the second identifier.

10. The computer-implemented method for processing image data as recited in claim 1, comprising creating the mask based on a purpose for obtaining image data.

11. The computer-implemented method for processing image data as recited in claim 10, wherein creating the mask comprises selecting the purpose for obtaining the image data from among a selection of purposes.

12. The computer-implemented method for processing image data as recited in claim 10, wherein the compressed image data and the multi-resolution mask comprise three-dimensional image data.

* * * * *